US012618057B2

(12) United States Patent
Kim et al.

(10) Patent No.: US 12,618,057 B2
(45) Date of Patent: May 5, 2026

(54) METHOD OF PURIFYING BOTULINUM TOXIN

(71) Applicant: JETEMA CO., LTD., Gangwon-do (KR)

(72) Inventors: Jae Young Kim, Seoul (KR); Jeong Sun Nam, Seoul (KR); Seungho Kim, Seoul (KR); Seung Kwan Choi, Gyeonggi-do (KR); Bum Jin Yun, Seoul (KR); Jin Hee Choi, Seoul (KR)

(73) Assignee: JETEMA CO., LTD., Gangwon-Do (KR)

( * ) Notice: Subject to any disclaimer, the term of this patent is extended or adjusted under 35 U.S.C. 154(b) by 741 days.

(21) Appl. No.: 17/603,326

(22) PCT Filed: Apr. 14, 2020

(86) PCT No.: PCT/KR2020/005041
§ 371 (c)(1),
(2) Date: Oct. 12, 2021

(87) PCT Pub. No.: WO2020/213928
PCT Pub. Date: Oct. 22, 2020

(65) Prior Publication Data
US 2022/0186201 A1 Jun. 16, 2022

(30) Foreign Application Priority Data
Apr. 15, 2019 (KR) ........................ 10-2019-0043868

(51) Int. Cl.
*C07K 1/18* (2006.01)
*C12N 9/52* (2006.01)

(52) U.S. Cl.
CPC ........ *C12N 9/52* (2013.01); *C12Y 304/24069* (2013.01)

(58) Field of Classification Search
None
See application file for complete search history.

(56) References Cited

U.S. PATENT DOCUMENTS

| | | | |
|---|---|---|---|
| 7,354,740 B2 | 4/2008 | Xiang et al. | |
| 7,452,697 B2 | 11/2008 | Luo et al. | |
| 2003/0008367 A1 | 1/2003 | Oguma | |
| 2018/0251741 A1 | 9/2018 | Kim et al. | |

FOREIGN PATENT DOCUMENTS

| | | |
|---|---|---|
| CN | 106117325 A | 11/2016 |
| JP | 2011074025 A | 4/2011 |
| KR | 1020070116710 A | 12/2007 |
| KR | 1020180037420 A | 4/2008 |
| KR | 10-2009-0120222 A | 11/2009 |
| KR | 1020120099431 A | 9/2012 |
| KR | 1020120105417 A | 9/2012 |
| KR | 10-1339349 B1 | 12/2013 |
| KR | 1020170062694 A | 6/2017 |
| RU | 2230325 C2 | 6/2004 |
| RU | 2627159 C2 | 8/2017 |
| RU | 2663136 C2 | 8/2018 |
| WO | WO2006042542 A2 | 4/2006 |
| WO | 2011008713 A1 | 1/2011 |
| WO | 2011050072 A1 | 4/2011 |
| WO | 2018065972 A1 | 4/2018 |
| WO | 2010127258 A1 | 11/2020 |

OTHER PUBLICATIONS

"Food Products: Methods for Detection of Botulinic Toxins and Clostridium Botulinum", Interstate Standard, 2010, Official Edition, Publisher: IPK Standards Publishing House.
English Translation, "Food Products: Methods for the Detection of Botulinic Toxins Clostridium Botulinum", Interstate Standard, 2010, Offical Edition, Publisher: IPK Standards Publishing House.
Office Action issued on Aug. 15, 2022 in counterpart Russian Patent Application No. 2021128381, Aug. 15, 2022.
English Translation of Office Action issued in counterpartRussian Patent Application No. 2021128381, Aug. 15, 2022.
Search Report issued on Aug. 15, 2022 in counterpart Russian Patent Application No. 2021128381, Aug. 15, 2022.
Johnson, S.K., et al., "Scale-up of the fermentation and purification of the recombinant heavy chain fragment C of botulinum neurotoxin serotype F, expressed in Pichia pastoris", Protein & Expression Purification, 2003, pp. 1-9, vol. 32, Publisher: Elsevier.
Kannan, K., et al., "Methods Development for the Biochemical Assessment of Neurobloc TM (Botulinum Toxin Type B)", Movement Disorders, 2000, pp. 18-26, vol. 15, No. 2, Publisher: Movement Disorders Society.
Schantz, E., et al., "Properties and Use of Botulinum Toxin and Other Microbial Neurotoxins in Medicine", Microbiological Reviewss, 1992, pp. 80-99, vol. 56, No. 1, Publisher: American Society for Microbiology.
Schmidt, J., et al., "Purification of Type E Botulinum Neurotoxin by High-Performance Ion Exchange Chromatography", Analytical Biochemistry, 1986, pp. 213-219, vol. 156.
Zhou, L., et al., "Expression and Purification of the Light Chain of Botulinum Neurotoxin A: A Single Mutation 5 Abolishes Its Cleavage of SNAP-25 and Neurotoxicity after Reconstitution with the Heavy Chain", Biochemistry, 1995, pp. 15175-15181, vol. 34, Publisher: American Chemical Society.

(Continued)

*Primary Examiner* — Richard G Hutson
(74) *Attorney, Agent, or Firm* — HULTQUIST, PLLC; Steven J. Hultquist

(57) ABSTRACT

Disclosed is a method of purifying a botulinum toxin including (a) pre-treating a culture solution containing a botulinum toxin, (b) purifying the pre-treated botulinum toxin using anion exchange chromatography and (c) purifying the botulinum toxin using cation exchange chromatography. The method is capable of purifying a botulinum toxin with high purity and activity using a simple process including anion exchange chromatography and cation exchange chromatography, and is thus useful for botulinum toxin production.

2 Claims, 5 Drawing Sheets

(56)         References Cited

OTHER PUBLICATIONS

EESR Issued in counterpart European Patent Application No. 20791856. 6, Dec. 19, 2022.
Notice of Allowance issued in counterpart Korean Patent Application No. 10-2020-0044718, Dec. 26, 2022.
English Translation of Notice of Allowance Issued in counterpart Korean Patent Application No. 10-2020-0044718, Dec. 26, 2022.
Notice of Allowance Issued in Korean Patent Application No. 10-2020-0044716 on Mar. 23, 2023.
English Translation of Notice of Allowance Issued in Korean Patent Application No. 10-2020-0044716 on Mar. 23, 2023.

R : Reduced

NR : Non-Reduced

| | RT | Area | % Area | Height |
|---|---|---|---|---|
| 1 | 7.796 | 1930269 | 99.65 | 42668 |
| 2 | 10.142 | 6737 | 0.35 | 106 |

|   | RT | Area | % Area | Height | K Prime | Resolution | Symmetry Factor | USP Plate Count |
|---|------|---------|--------|--------|---------|------------|-----------------|-----------------|
| 1 | 8.862 | 1067372 | 95.53 | 25844 | 0.772 |  | 1.198 | 1066 |
| 2 | 10.304 | 49923 | 4.47 | 2008 | 1.061 | 1.655 |  | 3808 |

| | RT | Area | % Area | Height |
|---|---|---|---|---|
| 1 | 6.691 | 74989 | 3.66 | 2080 |
| 2 | 7.656 | 1932824 | 94.27 | 39254 |
| 3 | 9.350 | 20136 | 0.98 | 598 |
| 4 | 11.976 | 12441 | 0.61 | 325 |
| 5 | 13.776 | 9867 | 0.48 | 660 |

METHOD OF PURIFYING BOTULINUM TOXIN

CROSS-REFERENCE TO RELATED APPLICATIONS

This is a United States national phase under 35 USC § 371 of International Patent Application No. PCT/KR20/05041 filed Apr. 14, 2020, which in turn claims priority under 35 USC § 119 of Korean Patent Application No. 10-2019-0043868 filed Apr. 15, 2019. The disclosures of all such applications are hereby incorporated herein by reference in their respective entireties, for all purposes.

BACKGROUND OF THE INVENTION

Field of the Invention

The present invention relates to a method for purifying a botulinum toxin, and more specifically to a purification method capable of obtaining a botulinum toxin at high purity through a simple process of anion exchange chromatography and cation exchange chromatography.

Description of the Related Art

Botulinum toxin is a neurotoxic protein produced by bacteria such as *Clostridium butyricum, Clostridium baratii*, and *Clostridium botulinum*. Botulinum toxin blocks neuromuscular transmission and causes neuroparalytic diseases in humans and animals. In particular, botulinum toxin type A is known to be very fatal to humans. In addition to botulinum toxin type A, seven other botulinum toxins types, namely B, Cl, D, E, F, G and H, have been identified. Each botulinum toxin type is distinguished by a corresponding type-specific antibody, and there is a difference in the severity of the paralysis caused thereby and the animal species affected thereby.

The molecular weight of the botulinum toxin protein molecule is about 150 kDa, including a light chain of about 50 kDa and a heavy chain of about 100 kDa conjugated thereto. However, botulinum toxin released from *Clostridium* bacteria is released in the form of a complex of a 150 kDa toxin protein with at least one non-toxin protein. For example, botulinum toxin is released as 900 kDa, 500 kDa and 300 kDa complexes.

Botulinum toxin may be very fatal to humans, but botulinum toxin has recently been developed to treat a variety of symptoms including neuromuscular disorders characterized by skeletal muscle hyperactivity. For example, Botox® is a trademark of botulinum toxin A commercially developed by Allergan, Inc., which is used to alleviate or treat blepharospasm, strabismus, cervical dystonia and glabella (facial) wrinkles, and research is underway to develop applications suitable for other serotypes and clinically utilize the serotypes.

Botulinum toxins for clinical use are generally isolated from cell cultures. In this case, a variety of purification methods are used.

For example, botulinum toxin is purified in a complexed form by a series of precipitation and tangential flow filtration steps. [see: for example, Schantz E. J. et al., Microbiol. Rev. 1992 March 56 (1): 80-99]. However, this method typically provided a relatively low yield of less than about 10%. Other methods used include size exclusion, ion exchange and/or affinity chromatography [see, e.g., Schmidt J. J. et al., Anal.

Biochem. 1986 July; 156 (1): 213-219; Kannan K. et al., Mov. Disord. 2000; 15 (Suppl 2):20 (2000); and US Patent No. 2003/0008367].

Another method is independent synthesis of one of the heavy or light chains of botulinum toxin by recombinant means, rather than a complete and biologically active botulinum toxin protein [see e.g., Zhou L. et al., Biochemistry 1995; 34 (46): 15175-81 (1995); and Johnson S. K. et al., *Protein Expr. and Purif.* 2003; 32: 1-9 (2003)]. However, these methods disadvantageously require an additional step of reforming a complete and biologically active botulinum toxin protein.

More recent methods involve the use of hydrophobic interaction chromatography, mixed-mode and/or ion exchange chromatography to purify botulinum toxins as complexes (see, e.g., U.S. Pat. Nos. 7,452,697 and 7,354,740).

However, there is still a need in the technical art for an improved purification method for isolating complete botulinum toxins that are stable and biologically active. Accordingly, as a result of extensive efforts to develop a purification method for isolating highly pure botulinum toxins in a simplified manner, the present inventors found that a highly pure botulinum toxin can be produced using a simplified process of anion exchange chromatography and cation exchange chromatography, and in particular, a botulinum toxin can be purified to a purity of 95% or more using a Q column as an anion exchange resin and using an SP column as a cation exchange resin. Based on this finding, the present invention has been completed.

PRIOR ART DOCUMENT

Patent Document

US Patent Laid-open No. 2003/0008367
U.S. Pat. No. 7,452,697
U.S. Pat. No. 7,354,740

Non-Patent Document

Schantz E J, et al, Properties and use of botulinum toxin and other microbial neurotoxins in medicine, Microbiol. Rev. 1992 March 56(1):80-99
Schmidt J. J., et al., Purification of type E botulinum neurotoxin by high-performance ion exchange chromatography, Anal. Biochem. 1986 July; 156(1):213-219
Kannan K. et al., Methods development for the biochemical assessment of NeuroBloc (botulinum toxin type B), Mov. Disord. 2000; 15(Suppl 2):20
Wang Y. C., The preparation and quality of botulinum toxin type A for injection (BTXA) and its clinical use, Dermatol. Las. Faci. Cosm. Surg. 2002; 58
Zhou L. et al., Expression and purification of the light chain of botulinum neurotoxin A: A single mutation abolishes its cleavage of SNAP-25 and neurotoxicity after reconstitution with the heavy chain, Biochemistry 1995; 34(46):15175-81
Johnson S. K., et al., Scale-up of the fermentation and purification of the recombination heavy-chain fragment C of botulinum neurotoxin serotype F expressed in *Pichia pastoris, Protein Expr. and Purif.* 2003; 32: 1-9

SUMMARY OF THE INVENTION

Therefore, the present invention has been made in view of the above problems, and it is an object of the present invention to provide a method for purifying a botulinum toxin at a very high purity using a simple process.

In accordance with an aspect of the present invention, the above and other objects can be accomplished by the provision of a method of purifying a botulinum toxin comprising (a) pre-treating a culture solution containing a botulinum toxin, (b) purifying the pre-treated botulinum toxin using anion exchange chromatography, and (c) purifying the botulinum toxin using cation exchange chromatography.

Effects of the Invention

The present invention can improve the purity of a botulinum toxin after purification, in particular, can purify a botulinum toxin of 900 kDa using only a simple process including anion exchange chromatography and cation exchange chromatography, and is thus useful for botulinum toxin production.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
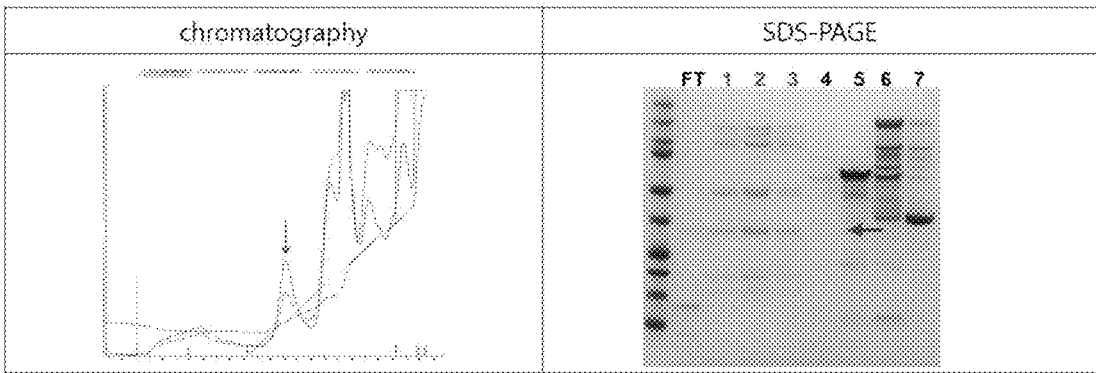
FIG. 1 shows the result of FPLC and SDS-PAGE analysis of a botulinum toxin in an eluent after anion exchange chromatography according to an embodiment of the present invention.

Unless defined otherwise, all technical and scientific terms used herein have the same meanings as appreciated by those skilled in the field to which the present invention pertains. In general, the nomenclature used herein is well-known in the art and is ordinarily used.

In the present invention, it was identified that, when a botulinum toxin culture solution is purified through a purification process using anion exchange chromatography and cation exchange chromatography, a botulinum toxin in a uniform form of about 900 kDa can be isolated and purified at a high purity compared to a botulinum toxin prepared by a conventional method. In particular, it was identified that, when using a Q column as an anion exchange resin and an SP column as a cation exchange resin, a botulinum toxin can be purified to a purity of 95% or more.

Accordingly, in one aspect, the present invention is directed to a method of purifying a botulinum toxin comprising (a) pre-treating a culture solution containing a botulinum toxin, (b) purifying the pre-treated botulinum toxin using anion exchange chromatography, and (c) purifying the botulinum toxin using cation exchange chromatography.

In the present invention, the anion exchange chromatography is preferably carried out using a Q column, and the cation exchange chromatography is preferably carried out using an SP column.

In the present invention, the Q column is a column packed with a material containing a quaternary ammonium (Q) functional group, and the SP column is a column packed with a material containing a sulfopropyl functional group.

The culture solution containing a botulinum toxin in step (a) of the present invention may be a culture solution of a *Clostridium botulinum* strain obtained using a conventional method known in the art, and may be obtained by culturing using a conventional medium used for culture, in particular, using a medium excluding an animal-derived component, preferably for example a PYG medium (containing potato peptone 3%, yeast extract 1% and glucose 1%).

The botulinum toxin-producing strain used in the present invention may be *Clostridium botulinum* or a variant thereof, and most preferably *Clostridium botulinum* type A, NCTC13319, but is not limited thereto. It will be apparent to those skilled in the art that any strain capable of producing a botulinum toxin can be used.

In a specific embodiment, the pre-treatment of the culture solution in step (a) of the present invention may be acid precipitation or ultrafiltration of the culture solution subjected to sterilization (by for example depth filtration and/or sterilization filtration), but is not limited thereto.

Acid precipitation may be precipitation using sulfuric acid or precipitation using hydrochloric acid, but is not limited thereto. That is, the acid precipitation in step (a) of the present invention may be acid precipitation of a culture solution containing a botulinum toxin using an acid such as sulfuric acid in one embodiment or hydrochloric acid in another embodiment, such that, after completion of the culture, the pH is adjusted to 3.0 to 4.5, preferably 3.3 to 4.0, and most preferably 3.4 to 3.6.

An ultrafiltration membrane may be a cassette type or a hollow fiber, but is not limited thereto. That is, in the step (a) of the present invention, the ultrafiltration may be ultrafiltration using a membrane with a size of 50 kDa to 500 kDa, preferably 100 kDa to 300 kDa, to collect a culture solution containing a botulinum toxin.

In addition, DNase, RNase, nuclease and/or Benzonase may be optionally used in order to remove nucleic acids during the pretreatment, but the invention is not limited thereto.

The present invention may include additional clarification in order to increase the resultant purity of the botulinum toxin. The clarification in the present invention is a step for additionally removing impurities after pre-treatment, and may be carried out by a conventional process such as known microfiltration, ultrafiltration, precision filtration or depth filtration. In one embodiment of the present invention, microfiltration may be performed using 0.1 to 0.4 μm hollow fibers.

In step (b) of the present invention, the anion exchange chromatography includes binding, to an anion exchange chromatography column, the pre-treated botulinum toxin dissolved in a buffer having a suitable concentration and pH for the binding of the botulinum toxin to the column, and then performing elution using a buffer solution having an increased salt concentration. In the anion exchange chromatography, a botulinum toxin having a non-complex form is removed.

In the method for purifying a botulinum toxin according to the present invention, the column used for anion exchange chromatography is preferably a column packed with a resin having a quaternary ammonium (Q) functional group, and more preferably a Q column.

In the present invention, from the viewpoint of removing impurities and keeping the botulinum toxin highly active, the anion exchange chromatography in step (b) may be carried out using a Q column, preferably a Toyopearl SuperQ 650M column, a Q sepharose FF column, a Q Sepharose High-Performance (Q Sepharose HP) column or the like, more preferably, a Toyopearl SuperQ 650M column or a Q sepharose FF column.

In the present invention, the Toyopearl SuperQ 650M column is a column packed with a resin containing a methacrylic bead with a particle size of 65 μm comprising a quaternary ammonium (Q) functional group, the ion exchange capacity of the column is 0.25±0.05 meq/mL, and the DBC (dynamic binding capacity) of the column is 149 mg/mL based on BSA.

In the present invention, the Q FF column is a strong anion exchanger containing a quaternary ammonium (Q) functional group and having a particle size of 90 μm, the ion exchange capacity of the column is 0.18 to 0.25 mmol Cl⁻/mL, and the DBC of the column is 120 mg/mL based on HAS.

In step (b), the botulinum toxin may be dissolved in a 30 to 70 mM sodium phosphate buffer having a pH of 5.0 to 7.0, preferably a pH of 5.5 to 6.5, and then injected into the Q column, but is not limited thereto.

In step (b), the botulinum toxin bound to the column may be eluted with a 30 to 70 mM sodium phosphate buffer having a pH of 5.0 to 7.0, preferably a pH of 5.5 to 6.5, supplemented with 0.4 to 0.6M sodium chloride, but is not limited thereto.

In the method for purifying a botulinum toxin according to the present invention, the cation exchange chromatography column is preferably a column equipped with a resin containing a sulfopropyl (SP) functional group, and more preferably an SP column.

In the present invention, from the viewpoint of removing impurities and keeping the botulinum toxin highly active, the cation exchange chromatography in step (c) may be carried out using an SP column, preferably an SP sepharose HP column, SP sepharose FF column, Capto S column or the like.

The botulinum toxin-containing fraction eluted through the anion exchange chromatography in step (c) may be dissolved in a 15 to 25 mM sodium citrate buffer having a pH of 3.5 to 5.5, preferably a pH of 4.0 to 5.0, and may then be injected into the SP column, but is not limited thereto.

In the present invention, the SP sepharose HP column is a column packed with a resin that contains a sulfopropyl functional group, has a 6% spherical, cross-linked agarose matrix form, and has a DBC of 55 mg/mL based on ribonuclease A and a particle size of 34 μm.

In the present invention, the SP sepharose FF column is a column packed with a resin that contains a sulfopropyl functional group, has a 6% highly cross-linked agarose matrix form and has a DBC of 70 mg/mL based on ribonuclease A and a particle size of 90 μm.

In step (c), the botulinum toxin may be eluted with a 15 to 25 mM sodium citrate buffer having a pH of 3.5 to 5.5, preferably a pH of 4.0 to 5.0, supplemented with 0.4 to 0.6M sodium chloride, but is not limited thereto.

The botulinum toxin purified by the method described above may be a botulinum toxin type A having a purity of at least 95%, and the purified botulinum toxin may have a higher purity than a botulinum toxin purified by a conventional method.

The botulinum toxin may be derived from *Clostridium botulinum* type A, NCTC13319, but is not limited thereto.

As used herein, the term "fraction" refers to a group of passing-through substances containing at least one target molecule, which are each separated and collected by a separation method, wherein the at least one target molecule (such as a botulinum toxin) contained along with one or more impurities in a biopharmaceutical agent passes through a substance binding to the one or more impurities and the target molecule usually does not bind to the substance (i.e., flows through the substance) or binds thereto and is then eluted.

As used herein, the term "purification" refers to an operation of increasing the purity by removing co-existing impurities from a certain substance and in this specification, purification refers to isolation of a botulinum toxin produced when overgrown botulinum bacteria die, from a culture solution of botulinum bacteria, and means a process for improving a purity during a botulinum toxin production process.

EXAMPLE

Hereinafter, the present invention will be described in more detail with reference to examples. However, it will be obvious to those skilled in the art that these examples are provided only for illustration of the present invention and should not be construed as limiting the scope of the present invention.

Example 1. Preparation of Samples and Experimental Materials 1-1. Sample Preparation The botulinum strain used in the present invention was *Clostridium botulinum* type A, NCTC13319, and the strain was primarily inoculated into 500 mL PYG medium (potato peptone 3%, yeast extract 1%, glucose 1%) and cultured under anaerobic conditions at 34±1° C. in a ReadytoProcess WAVE 25 incubator for 12 hours to 24 hours. After culturing, when the growth of the strain reached the log phase, 100 mL of the strain was inoculated into 5 L PYG medium and cultured under anaerobic conditions in a ReadytoProcess WAVE 25 incubator for 40 to 72 hours. The culture solution was sterilized using a sterilizing filter, and only the culture solution was recovered. The culture solution was titrated to pH 3.5 using 3N sulfuric acid, precipitation was observed, and then the result was stored in a refrigerated state for 16 hours or more.

1-2. Preparation of Experimental Materials

The experimental materials used in the present invention were as follows: purified water (ultrapure water or water with quality equal to or higher than ultrapure water), TOYO-PEARL® SuperQ 650M hydrophilic polymer gel (Tosoh Bioscience, 43205), SP SEPHAROSE® HP high molecular weight gel (GE Healthcare, 171087), Q SEPHAROSE® FF high molecular weight gel (GE Healthcare, 170510), SP SEPHAROSE® FF high molecular weight gel (GE Healthcare, 170729), butyl SEPHAROSE® FF high molecular weight gel (GE Healthcare, 170980), phenyl SEPHAR- OSE® HP high molecular weight gel (GE Healthcare, 171082), citric acid (Merck, 1.37002.5000), trisodium citrate dehydrate (Merck, 1.37042.5000), sodium phosphate monobasic (Merck, 1.06349.1000), sodium phosphate dibasic (Merck, 1.06585), sodium chloride (Merck, 1.37017.5000).

Example 2. Purification of Botulinum Toxin 2-1. Microfiltration

Microfiltration equipment, AKTA flux 6 (GE Healthcare) was turned on and 0.2 μm hollow fibers were connected thereto. 5 L of distilled water was added thereto, and the equipment and hollow fibers were washed twice at TMP of 0.3 bar. 5 L of the sulfuric acid precipitate of botulinum toxin culture solution prepared in Example 1-1 was added to microfiltration equipment and concentrated to 1 L at TMP of 0.3, 2 L of DW was added to the concentrate, and concentration was repeated 5 times from 3 L to 1 L. 1 L of 50 mM sodium phosphate (pH 6.0) was added, and extraction was performed through circulation for 1 hour. The extract was recovered through a permeate line of the microfiltration equipment, and 300 kDa cut-off hollow fibers were connected to the microfiltration equipment. The extract was added thereto and concentrated to 500 mL at a TMP of 0.3 bar, recovered, and stored at 4° C.

2-2. Anion Exchange Chromatography

TOYOPEARL® SuperQ 650M resin was mounted in an AKTA Pure system. The column was equilibrated by flowing 108 mL (1 CV) of an equilibration/wash buffer (50 mM sodium phosphate, pH 6.0). 200 mL of the sample prepared in Example 2-1 was injected at 8 mL/min. After the injection, the column was washed with 216 mL (2 CV) of equilibration/wash buffer (50 mM sodium phosphate, pH 6.0). After washing, elution was performed with 5 CV of an equilibration/elution buffer at a 50% gradient (linear gradient) (see Table 1). A total of 14 fractions were sequentially obtained, and each of the fractions was identified by SDS-PAGE.

TABLE 1

| Column | Toyopearl SuperQ 650M |
| --- | --- |
| Binding and washing buffer | 50 mM sodium phosphate, pH 6.0 |
| Elution buffer | 50 mM sodium citrate/0.5M sodium chloride, pH 6.0 |

The results are shown in FIG. 1. HA33 (red arrow on SDS-PAGE) was detected from Fractions 1 to 3 of a total of 14 fractions, and the botulinum toxin in the form of a 900 kDa complex was purified from the corresponding fraction.

2-3. Cation Exchange Chromatography

A HiTrap SP column (GE Healthcare, 17115201) was mounted in an AKTA Pure system. The column was equilibrated by flowing 10 mL (2 CV) of an equilibration/wash buffer (20 mM sodium phosphate, pH 4.5). The sample (140 mL), prepared by collecting Fractions 1 to 3, containing a botulinum toxin, through SDS-PAGE in Example 2-2 was dialyzed at 20 mM sodium citrate at pH 4.5 and injected into the column at 5 mL/min. After the injection, the column was washed with 5 CV, 25 mL of equilibration/wash buffer (20 mM sodium citrate pH 4.5). After washing, elution was performed with 20 CV of an equilibration/elution buffer at 60% gradient (linear gradient) (see Table 2). A total of 21 fractions (5 mL each) were sequentially obtained, and each of the fractions was identified by SDS-PAGE.

TABLE 2

| Column | SP Sepharose HP |
| --- | --- |
| Binding and washing buffer | 20 mM sodium citrate, pH 4.5 |
| Elution buffer | 20 mM sodium citrate/0.5M sodium chloride, pH 4.5 |

Figure 2:
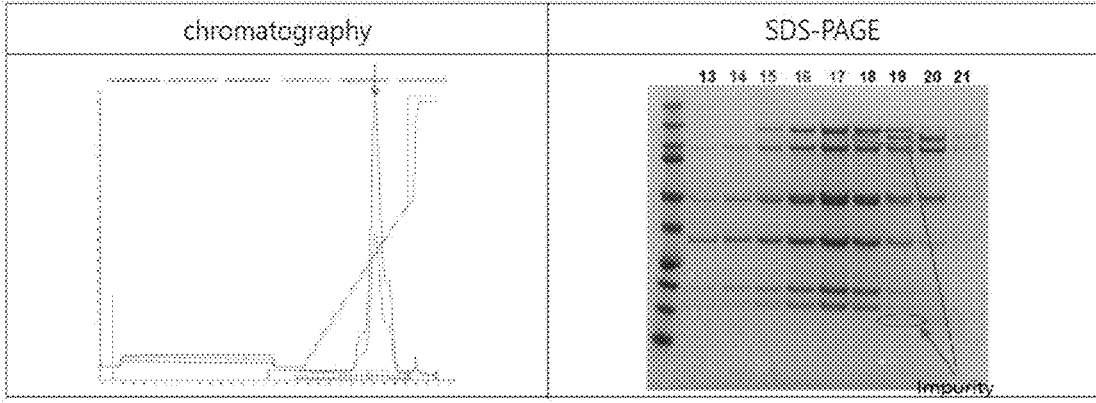
FIG. 2 shows the result of FPLC and SDS-PAGE analysis of a botulinum toxin in an eluent after cation exchange chromatography according to an embodiment of the present invention.

The results are shown in FIG. 2, and a botulinum toxin as a 900 kDa complex containing no impurities was detected from Fractions 14 to 17 among the total of 21 fractions.

2-4. Concentration

Among the fractions eluted by the cation exchange chromatography of Example 2-3, 20 mL of the Fractions 14 to 17 containing a botulinum toxin were collected, poured into a 30 kDa cut-off Centricon filter unit and concentrated to 0.5 mL under conditions of 4000×g and 4° C.

Example 3. Comparison Between Standard Product and Purified Product

The botulinum toxin purified in Example 2 and the commercially available botulinum toxin C-BoNT/A1 (Cat. No. #3102, miprolab) were each diluted to a concentration of 1 mg/ml in 50 mM sodium phosphate buffer (pH 6.2). Samples for loading were prepared under the reducing and non-reducing conditions shown in Table 3. The samples were subjected to electrophoresis in a 10-well Novex WedgeWell with 4-20% tris-glucine (Invitrogen, NP04200BOX), about 30 mL of Instant Blue stain reagent was added and the sample was stained on a shaker for 60 minutes. The staining reagent was completely removed, about 30 mL of purified water was added, and the sample was washed five or more times on a shaker for 30 minutes. When the background was sufficiently removed and the band could be detected, the gel was analyzed using an image analyzer.

TABLE 3

| | Reducing conditions | Non-reducing conditions |
| --- | --- | --- |
| Botulinum toxin (1 mg/ml) | 3 uL | 3 uL |
| LDS Sample Buffer (4x) | 5 uL | 5 uL |
| Sample Reducing Agent (10x) | 2 uL | 0 uL |
| Purified water | 10 uL | 12 uL |
| Total Volume | 20 uL | |

Figure 3:
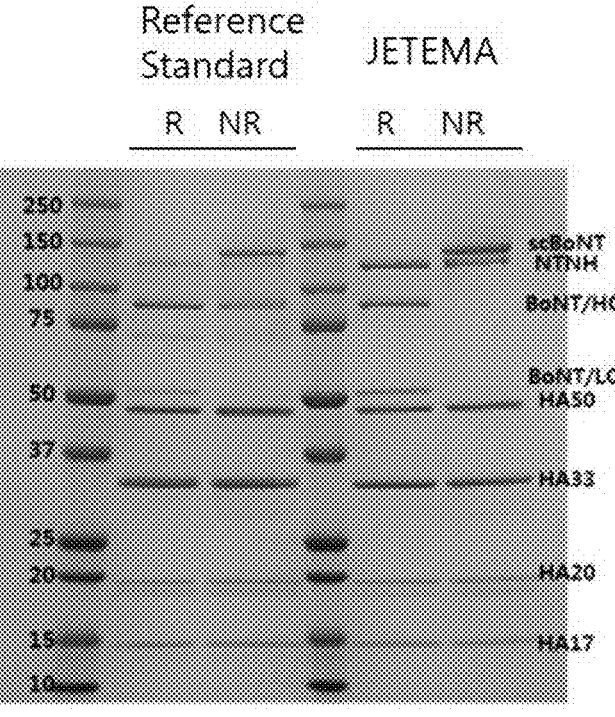
FIG. 3 shows the result of SDS-PAGE analysis to determine the purification effect of a botulinum toxin according to the present invention and a commercially available botulinum toxin.

As a result, as shown in FIG. 3, the botulinum toxin purified by the purification method of the present invention was identified in the same position as the commercially available botulinum toxin, which indicates that the purification method of the present invention can accurately purify only the target protein of interest. More impurity bands were detected in the standard product, C-BoNT, whereas neat and apparent bands were detected in the sample (Jetema) purified by the purification method of the present invention.

Example 4. Comparison of Purity with Two-Step Purification Process of Other Company The purity of botulinum toxin, purified in accordance with the purification method described in Korean Patent Application No. 10-2013-0092024, filed by Allergan Inc., a leading manufacturer of botulinum toxin, was analyzed.

The purity of the purified botulinum toxin was analyzed by HPLC using the conditions shown in Table 4.

TABLE 4

| Item | Condition |
| --- | --- |
| Column | PROTEIN KW-804 |
| Size | 8 mm × 300 mm |
| Stationary phase | silica gel for chromatography R (7 μm) |
| Temperature | 25° C. |
| Mobile phase | 50 mM Sodium phosphate pH 6.0, 0.15M NaCl |
| Flow rate | 1.0 mL/min |
| Running time | 30 min |
| Detection | UV detector, 278 nm |
| Injection volume | 20 μL |

Figure 5:
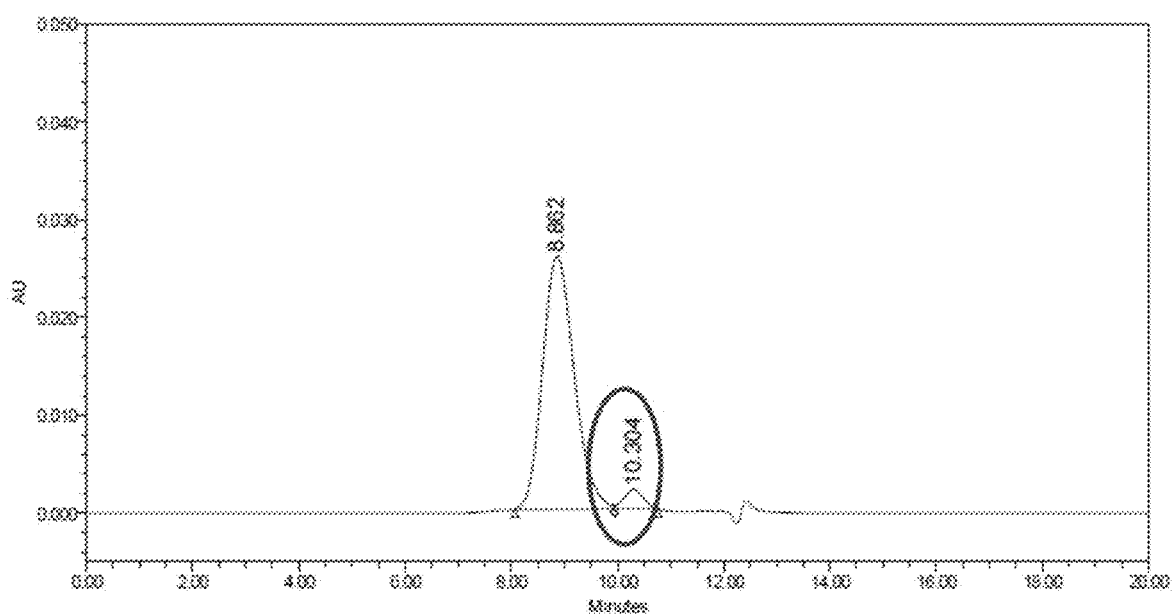
FIG. 5 shows the result of determination of the purity of the botulinum toxin purified by a purification method in accordance with Korean Patent Application No. 10-2013-0092024.

As a result, as shown in FIG. 5, smaller impurities (retention time, 10.3 min) were detected in addition to the main peak, and the 900 kDa protein was not effectively separated from the 150 kDa, 300 kDa or 500 kDa protein.

Figure 6:
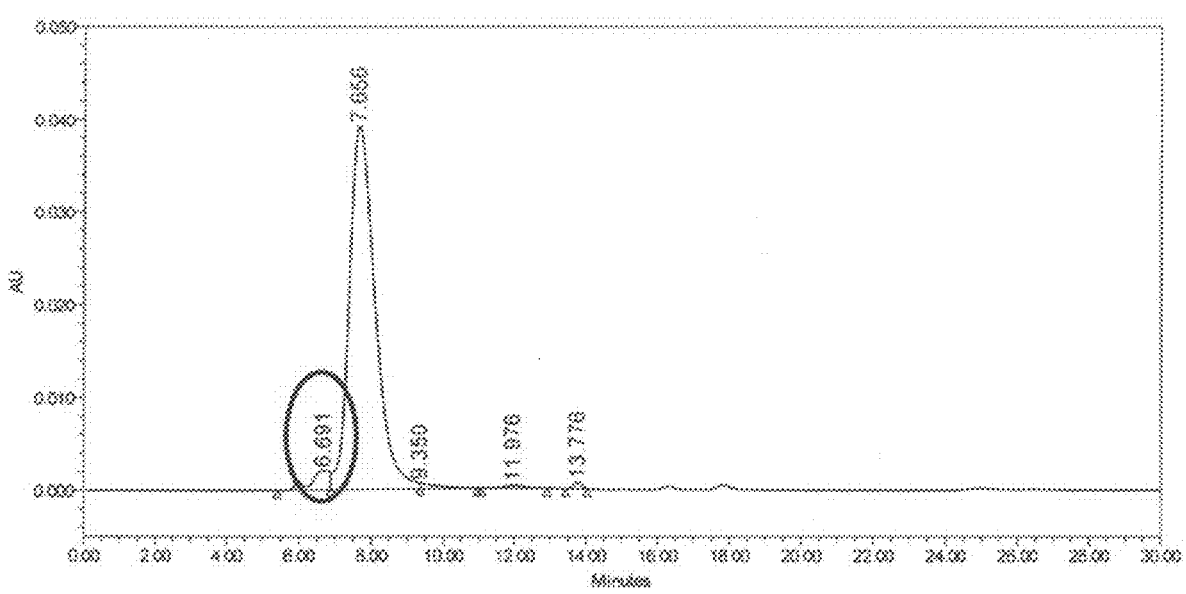
FIG. 6 shows the result of determination of the purity of the botulinum toxin purified by a purification method in accordance with U.S. patent application Ser. No. 11/932,789.

In addition, the purity of botulinum toxin purified in accordance with the purification method of U.S. patent application Ser. No. 11/932,789, filed by Allergan Inc., was analyzed. As a result, larger impurities (retention time, 6.7 min), were detected, in addition to the main peak, as shown in FIG. 6. This means that undesired precipitates were formed, and it can be expected that the purification process affected the protein structure.

Figure 4:
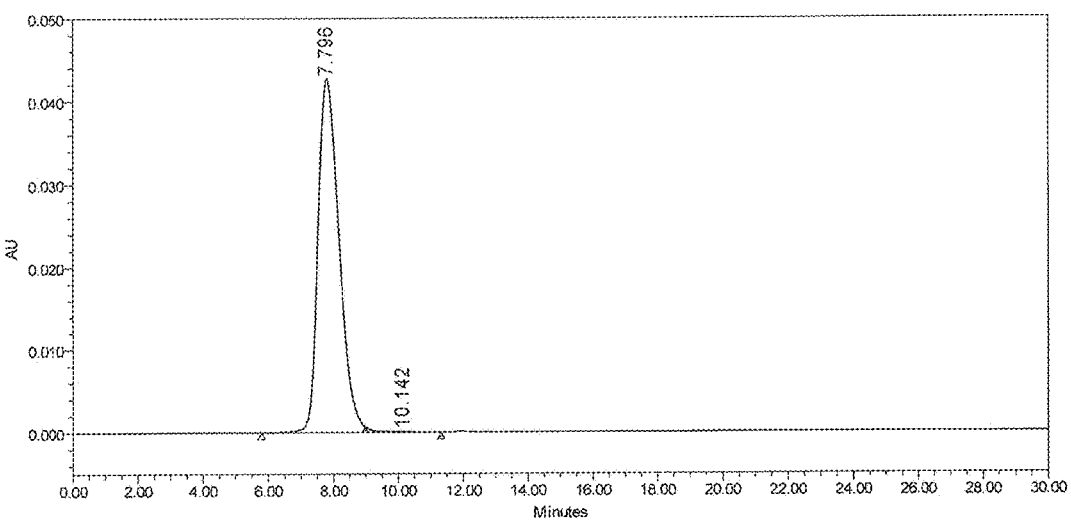
FIG. 4 shows the result of determination of the purity of the botulinum toxin purified according to the present invention.

On the other hand, as can be seen from the results of FIG. 4, the present invention enables specific purification only of toxins of about 900 kDa, and the modification of toxins during purification is also minimized.

Example 5. Comparison Between Two-Step Chromatography Process of Allergan and Purification Process of the Present Invention The purity and titer of purified botulinum toxin were compared between the purification methods using the resin used for the purification of botulinum toxin disclosed in U.S. Pat. No. 7,452,697 and US Patent Publication No. 2019-0201505 of Allergan Inc. and the purification methods of the present invention using different types of resins (Table 5).

The purity was detected by HPLC in accordance with the method of Table 4, and the titer was calculated by Probit statistical analysis using CombiStats based on the result of the number of dead mice for 3 days in a protein concentration of 1 mg/mL using a mouse assay.

TABLE 5

| | 1st column resin | 2nd column resin |
| --- | --- | --- |
| Present Invention<br><br>(Experimental Example 1) | TOYOPEARL® SuperQ 650M hydrophobic polymer gel | SP SEPHAROSE® HP high molecular weight gel |
| Present Invention<br><br>(Experimental Example 2) | Q SEPHAROSE® FF | SP SEPHAROSE® FF high molecular weight gel |
| U.S. Pat. No. 7,452,697<br><br>(Comparative Example 1) | Butyl SEPHAR-OSE® FF high molecular weight gel | SP SEPHAROSE® HP high molecular weight gel |
| US 2019-0201505<br><br>(Comparative Example 2) | SP SEPHAROSE® HP high moleclar weight gel | Phenyl SEPHAROSE® HP high molecular weight gel |

The types and purification conditions of the columns used respectively in Experimental Examples and Comparative examples are shown in Tables 6 to 9.

TABLE 6

| Experimental Example 1 (Toyopearl Super Q → SP-HP) | |
| --- | --- |
| Column | Toyopearl Super Q (Diameter: 2.6 cm, Height: 10 cm) |
| Column volume | 53 mL |
| Binding & washing buffer | 50 mM Sodium Phosphate 6.0 |
| Elution buffer | 50 mM Sodium Phosphate/1M Sodium Chloride, pH 6.0 |
| Elution condition | 0-0.25M Sodium Chloride, 5 CV |
| Column | SP-HP (Diameter: 0.66 cm, Height: 12.5 cm) |
| Column volume | 4.27 mL |
| Binding & washing buffer | 20 mM Sodium Citrate pH 4.5 |
| Elution buffer | 20 mM Sodium Citrate/0.5M Sodium Chloride, pH 4.5 |
| Elution condition | 0-0.3M Sodium Chloride, 20 CV |

TABLE 7

| Experimental Example 2 (Q-FF → SP-FF) | |
| --- | --- |
| Column | Q-FF (Diameter: 2.6 cm, Height: 10 cm) |
| Column volume | 53 mL |
| Binding & washing buffer | 50 mM Sodium Phosphate, 6.0 |
| Elution buffer | 50 mM Sodium Phosphate/0.5M Sodium Chloride, pH 6.0 |
| Elution condition | 0-0.5M Sodium Chloride, 5 CV |
| Column | SP-FF (Diameter: 0.66 cm, Height: 13 cm) |
| Column volume | 4.45 mL |
| Binding & washing buffer | 20 mM Sodium Citrate, pH 4.5 |
| Elution buffer | 20 mM Sodium Citrate/0.5M Sodium Chloride, pH 4.5 |
| Elution condition | 0-0.3M Sodium Chloride, 20 CV |

TABLE 8

| Comparative Example 1 (Butyl-FF → SP-HP) | |
| --- | --- |
| Column | Butyl-FF (Diameter: 2.6 cm, Height: 12 cm) |
| Column volume | 4.11 mL |
| Binding & washing buffer | 50 mM Sodium Phosphate/2M Sodium Chloride, pH 6.2 |
| Elution buffer | 50 mM Sodium Phosphate, pH 6.2 |
| Elution condition | 2-0M Sodium Chloride, 10 CV/0M Sodium Chloride, 5 CV |
| Column | SP-HP (Diameter: 0.66 cm, Height: 12.5 cm) |
| Column volume | 4.27 mL |
| Binding & washing buffer | 20 mM Sodium Citrate, pH 4.5 |
| Elution buffer | 20 mM Sodium Citrate/0.5M Sodium Chloride, pH 4.5 |
| Elution condition | 0-0.3M Sodium Chloride, 5 CV/1M Sodium Chloride, 3 CV |

TABLE 9

| Comparative Example 2 (SP-HP → Phenyl-HP) | |
| --- | --- |
| Column | SP-HP (Diameter: 5 cm, Height: 9.7 cm) |
| Column volume | 190 mL |
| Binding & washing buffer | 20 mM Sodium Citrate pH 4.5 |
| Elution buffer | 20 mM Sodium Citrate, 0.5M Sodium Chloride pH 4.5 |
| Elution condition | 0-0.3M Sodium Chloride 5 CV, 1M Sodium Chloride 3 CV |
| Column | Phenyl-HP (Diameter: 2.6 cm, Height: 12 cm) |
| Column volume | 46 mL |
| Binding & washing buffer | 50 mM Sodium Phosphate/2M Sodium Chloride, pH 6.2 |
| Elution buffer | 50 mM Sodium Phosphate, pH 6.2 |

TABLE 9-continued

| Comparative Example 2 (SP-HP → Phenyl-HP) | |
|---|---|
| Elution condition | 2-0M Sodium Chloride, 10 CV/0M Sodium Chloride, 5 CV |

As a result, as can be seen from Table 10, the botulinum toxin purified in accordance with Experimental Example 1, which is the purification method of the present invention, yielded a high purity of 98.6%, and the botulinum toxin purified in accordance with Experimental Example 2, which is a purification method using a different type of resin, had similar results (purity of 95.2%). Comparative Examples 1 and 2 which are purification methods described in the patent of Allergan Inc. were found to have a lower purity than the toxins purified by Experimental Examples 1 and 2. The titer of botulinum toxin was found to be high in all cases except for the toxin purified by the method of Comparative Example 1.

TABLE 10

| Step | | SEC-HPLC (Purity, %) | Titer (Unit/mg) |
|---|---|---|---|
| Experimental Example 1 | Toyopearl SuperQ 650M–> SP-HP | 98.6 | $3.17 \times 10^7$ |
| Experimental Example 2 | Q -FF –> SP-FF | 95.2 | $4.05 \times 10^7$ |
| Comparative Example 1 | Butyl-FF –> SP-HP | 63.1 | $1.10 \times 10^7$ |
| Comparative Example 2 | SP-HP –> Phenyl-HP | 82.7 | $4.16 \times 10^7$ |

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

What is claimed is:

1. A two column chromatography method of purifying a 900 kDa botulinum toxin complex, comprising:

(a) pre-treating a culture solution containing a botulinum toxin;

(b) preparing the pre-treated botulinum toxin from step (a) by dissolving it in 30-70 mM sodium phosphate buffer at pH 5.5-6.5 and injecting it into an anion exchange chromatography column to bind the botulinum toxin to the anion exchange chromatography medium at a pH higher than an isoelectric point (PI) of botulinum toxin, said anion exchange chromatography column comprising a column packed with a resin containing a methacrylic bead with a particle size of 65 μm comprising a quaternary ammonium (Q) functional group, wherein the ion exchange capacity of the column is 0.25±0.05 meq/mL, and the DBC (dynamic binding capacity) of the column is 149 mg/mL based on BSA, and separating the botulinum toxin, which is bound to the anion exchange chromatography medium, by elution with a 30 to 70 mM sodium phosphate buffer having a pH of 5.5 to 6.5 comprising 0.4 to 0.6M sodium chloride; and (c) preparing the botulinum toxin from step (b) by dissolving it in 15 to 25 mM sodium citrate buffer at pH 4.0 to 5.0 and injecting it into a cation exchange chromatography column to bind the botulinum toxin to the cation exchange chromatography medium, said cation exchange chromatography column comprising a column packed with a resin that contains a sulfopropyl functional group, has a 6% spherical, cross-linked agarose matrix form, and has a DBC of 55 mg/mL based on ribonuclease A and a particle size of 34 μm, and separating 900 kDa botulinum toxin complex from the solution which is bound to the cation exchange chromatography medium, by elution with a 15 to 25 mM sodium citrate buffer having a pH of 4.0 to 5.0 comprising 0.4 to 0.6M sodium chloride.

2. The method according to claim 1, wherein the purified botulinum toxin is botulinum toxin A having a purity of 95% or more.

* * * * *